United States Patent [19]
Freeman

[11] Patent Number: 6,060,463
[45] Date of Patent: May 9, 2000

[54] TREATMENT OF CONDITIONS OF ABNORMALLY INCREASED INTRAOCULAR PRESSURE BY ADMINISTRATION OF PHOSPHONYLMETHOXYALKYL NUCLEOSIDE ANALOGS AND RELATED NUCLEOSIDE ANALOGS

[75] Inventor: William R. Freeman, Del Mar, Calif.

[73] Assignee: William Freeman, Del Mar, Calif.

[21] Appl. No.: 09/154,490

[22] Filed: Sep. 16, 1998

Related U.S. Application Data

[63] Continuation of application No. 08/440,447, May 12, 1995, which is a continuation-in-part of application No. 08/360,995, Dec. 20, 1994, which is a continuation-in-part of application No. 08/222,128, Apr. 4, 1994, Pat. No. 5,468,752.

[51] Int. Cl.$^7$ ........................ A61K 31/675; A61K 31/505
[52] U.S. Cl. ............................ 514/81; 514/272; 514/912; 514/913
[58] Field of Search ............................ 514/81, 272, 912, 514/913

[56] References Cited

U.S. PATENT DOCUMENTS

| | | | |
|---|---|---|---|
| 4,230,708 | 10/1980 | De Clercq et al. | 424/253 |
| 4,328,803 | 5/1982 | Pape | 128/276 |
| 4,517,925 | 5/1985 | Bracke et al. | 435/101 |
| 4,522,811 | 6/1985 | Eppstein et al. | 514/2 |
| 4,605,658 | 8/1986 | Holý et al. | 514/261 |
| 4,724,233 | 2/1988 | De Clercq et al. | 514/81 |
| 4,846,172 | 7/1989 | Berlin | 128/301.1 |
| 5,039,797 | 8/1991 | Clack et al. | 536/49 |
| 5,047,533 | 9/1991 | Reist et al. | 544/244 |
| 5,116,868 | 5/1992 | Chen et al. | 514/546 |
| 5,142,051 | 8/1992 | Holy et al. | 544/243 |
| 5,214,080 | 5/1993 | Iwamura et al. | 523/336 |
| 5,229,127 | 7/1993 | McKinzie | 424/427 |
| 5,273,056 | 12/1993 | McLaughlin et al. | 128/898 |
| 5,273,751 | 12/1993 | Dubroff | 424/427 |
| 5,278,126 | 1/1994 | Katano et al. | 503/201 |
| 5,282,851 | 2/1994 | Jacob-LaBarre | 623/6 |
| 5,292,362 | 3/1994 | Bass et al. | 106/124 |
| 5,302,585 | 4/1994 | Yu et al. | 514/81 |
| 5,468,752 | 11/1995 | Freeman | 514/272 |
| 5,869,468 | 2/1999 | Freeman | 514/81 |

FOREIGN PATENT DOCUMENTS

| | | |
|---|---|---|
| 0253412 | 7/1987 | European Pat. Off. . |
| 0253412A2 | 1/1988 | European Pat. Off. . |
| 9416101 | 7/1994 | WIPO . |
| 9417405 | 8/1994 | WIPO . |
| 9513821 | 5/1995 | WIPO . |
| 9519776 | 7/1995 | WIPO . |
| 9526734 | 10/1995 | WIPO . |
| 9527510 | 10/1995 | WIPO . |

OTHER PUBLICATIONS

Banker et al., "Influence of intravitreal injecions of HPMPC and related nucleoside analogs on intraocular pressure of guinea pig eyes," Abstract, Annual Meeting of the Association for Research in Vision and Ophthalmology, Fort Lauderdale, Florida, Apr. 1996.

Andrei, et al,. "Comparative Activity of Selected Antiviral Compounds against Clinical Isolates of Human Cytomegalovirus," *Eur. J. Clin. Microbiol. Infect. Dis.* 10(12):1026–1033 (1991).

Andreoli, et al., editors, *Cecil Essentials of Medicine* W.B. Saunders Company, publishers, pp. 690–691 (1986).

Assil and Weinreb, "Multivesicular Liposomes—Sustained Release of the Antimetabolite Cytarabine in the Eye," *Arch. Ophthalmol.* 105:400–403 (1987).

Berthe, et al., "Toxicologic and Pharmacokinetic Analysis of Intravitreal Injections of Foscarnet, Either Alone or in Combination With Ganciclovir," *Invest. Ophthal. & Visual Sci.* 35(3);1038–1045 (1994).

Cantrill, et al., "Treatment of Cytomegalovirus Retinitis with Intravitreal Ganciclovir," *Ophthalmology* 96(3):367–374 (1989).

Chemical Abstract 119:151515, Antivirals for the treatment of herpesvirus infections. DeClercq, Erik, *J. Antimicrob. Chemother.*, 32(Supple. A), 121–32 (English) 1993.

De Clercq, "Broad–Spectrum Anti–DNA Virus and Anti–Retrovirus Activity of Phosphonylmethoxyalkylpurines and –Pyrimidines," *Biochem. Pharm.* 42(5):963–972 (1991).

De Clercq, Erik, "Antivirals for the treatment of herpesvirus infections," *J. Antimicrobial Chemotherapy* 32(A):121–132 (1993).

Díaz–Llopis, et al., "Intravitreal Foscarnet for Cytomegalovirus Retinitis in a Patient With Acquired Immunodeficiency Syndrome," *American J. of Ophthalmology* 115(5):686–688 (1993).

Dolnak, et al., "Lack of Retinal Toxicity of the Anticytomegalovirus Drug (S)–1–(3–Hydroxy–2–Phosphonylmethoxypropyl) Cytosine," *Investigative Ophthalmology & Visual Science* 33(5):1557–1563 (Apr. 1992).

Flores–Aquilar, et al., "Long–Acting Therapy of Viral Retinitis with (S)–1–(3–Hydroxy–2–Phosphonylmethoxypropyl)cytosine," *J. of Infec. Diseases* 69(3):642–647 (Mar. 1994).

(List continued on next page.)

*Primary Examiner*—Zohreh Fay
*Attorney, Agent, or Firm*—Stephanie L. Seidman; Heller Ehrman White & McAuliffe

[57] ABSTRACT

Methods for treatment of conditions of abnormally increased intraocular pressure, particularly those caused by glaucoma, by administration of phosphonylmethoxyalkyl nucleoside analogs are provided. Compositions formulated and packaged for intraocular administration for use in the methods are also provided. Administration of the compound may be by intravitreal injection, aqueous humor injection, injection into the external layers of the eye, such as subconjunctival injection or subtenon injection, or may be, when penetrating derivatives are used, by topical application to the eye. The degree of reduction in pressure is dosage-dependent, and significant reduction in pressure is obtained. A single injection can produce prolonged, and perhaps permanent, lowering of the intraocular pressure.

37 Claims, No Drawings

OTHER PUBLICATIONS

Freeman, et al., "HPMPC for the Long Acting Treatment of Experimental Herpes Simplex Retinitis in Rabbits," 292:11:30 (Abstract), Investigative Ophthalmology & Visual Science, Annual Meeting Abstract Issue, May 3–8, 1992, Sarasota, FL.

Freeman, "Intraocular Antiviral Therapy," *Arch. Ophthalmol.* 107:1737–1739 (1989).

Friberg and Paul, "CMV Retinitis and Immunosuppression with FK506," *Retina/Anatomy & Pathology/Clinical Res./Immunology & Microbiology Paper Presentation 291*:11:15 (Abstract), Investigative Ophthalmology & Visual Science, Annual Meeting Abstract Issue, May 3–8, 1992, Sarasota, FL.

Gross, et al., "Longitudinal Study of Cytomegalovirus Retinitis in Acquired Immune Deficiency Syndrome," *Ophthalmology* 97:681–686 (1990).

Henderly, et al., "Cytomegalovirus Retinitis and Response to Therapy With Ganciclovir," *Opthalmology* 94(4):425–434 (1987).

Henry, et al., "Use of Intravitreal Ganciclovir (Dihydroxy Propoxymethyl Guanine) for Cytomegalovirus Retinitis in a Patient With Aids," *Am. J. Ophthal.* 103(1):17–23 (1987).

IUPAC–IUB Commission on Biochemical Nomenclature Symbols for Amino–Acid Derivatives and peptides Recommendations (1971), *Biochemistry* 11(9):17261732 (1972).

Jab, "Treatment of Cytomegalovirus Retinitis—1992," *Arch. Ophthalmol.* 110:185–187 (1992).

Kim, et al., "Preparation of Multivesicular Liposomes," *Biochimica et Biophysica Acta* 728:339–348 (1983).

Leibrandt, editor, *Professional Guide to Disease*, pp. 1203–1206 (1982).

Li, et al., "Activity of (S)–1–(3–hydroxy–2–phosphonylmethoxypropyl)cytosine (HPMPC) against guinea pig cytomegalovirus infection in cultured cells and in guinea pigs," *Antiviral Research* 13:237–252 (1990).

Maudgal and De Clercq, "(S)–1(–3–Hydroxy–2–Phosphonyl–Methoxypropyl)Cytosine in the Therapy of Thymidine Kinase–Positive and –Deficient Herpes Simplex Virus Experimental Keratitis," *Investigative Ophthalmol. & Visual Sci.* 32(6):1816–1820 (1991).

Maudgal, et al., "Effects of phosphonylmethoxyalkyl–purine and –pyrimidine derivatives on $TK^+$ and $TK^-$ HSV–1 keratitis in rabbits," *Antiviral Research* 16(1):93–100 (Jul. 1991).

Neyts, et al., "Efficacy of (S)–1–(3–Hydroxy–2–Phosphonylmethoxypropyl)Cytosine and 9–(1,3–Dihydroxy–2–Propoxymethyl)Guanine for the Treatment of Murine Cytomegalovirus Infection in Severe Combined Immunodeficiency Mice," *J. Med. Virol.* 37:67–71 (1992).

Neyts, et al., "Selective Inhibition of Human Cytomegalovirus DNA Synthesis by (S)–1–(3–Hydroxy–2–phosphonylmethoxypropyl)cytosine ([(S)–HPMPC] and 9–(1, 3–Dihydroxy–2–propoxymethyl)guanine (DHPG)," *Virology* 179:41–50 (1990).

Nogrady, "Medicinal Chemistry: A Biochemical Approach," Oxford Univ. Press, N.Y., pp. 388–392 (1985).

Sarraf, et al., "Transscleral Iontophoresis of Foscarnet," *American J. of Ophthalmology* 115:748–754 (1993).

Sanborn, et al., "Sustained–Release Ganciclovir Therapy for Treatment of Cytomegalovirus Retinitis," *Arch. Ophthalmol.* 110:188–195 (1992).

Shigeta, et al., "Comparative Inhibitory Effects of Nucleoside Analogues on Different Clinical Isolates of Human Cytomegalovirus in Vitro," *J. of Infectious Diseases* 163:270–275 (1991).

Smith, et al., "Intravitreal Sustained–Release Ganciclovir," *Arch. Ophthalmol.* 110:255–258 (1992).

Ussery, et al., "Intravitreal Ganciclovir in the Treatment of AIDS–associated Cytomegalovirus Retinitis," *Ophthalmology* 95(5):640–648 (1988).

TREATMENT OF CONDITIONS OF ABNORMALLY INCREASED INTRAOCULAR PRESSURE BY ADMINISTRATION OF PHOSPHONYLMETHOXYALKYL NUCLEOSIDE ANALOGS AND RELATED NUCLEOSIDE ANALOGS

RELATED APPLICATIONS

This application is a continuation of U.S. application Ser. No. 08/440,447 to William Freeman, filed May 12, 1995, entitled TREATMENT OF CONDITIONS OF ABNORMALLY INCREASED INTRAOCULAR PRESSURE BY ADMINISTRATION OF PHOSPHONYLMETHOXYALKYL NUCLEOSIDE ANALOGS AND RELATED NUCLEOSIDE ANALOGS. U.S. application Ser. No. 08/440,447 is a continuation-in-part of U.S. application Ser. No. 08/360,995 to William Freeman, filed Dec. 20, 1994, entitled TREATMENT OF CONDITIONS OF ABNORMALLY INCREASED INTRAOCULAR PRESSURE BY ADMINISTRATION OF PHOSPHONYLMETHOXYALKYL NUCLEOSIDE ANALOGS AND RELATED NUCLEOSIDE ANALOGS, and is also a continuation-in-part of U.S. application Ser. No. 08/222,128 to William Freeman, filed Apr. 4, 1994, entitled TREATMENT OF CONDITIONS OF ABNORMALLY INCREASED INTRAOCULAR PRESSURE BY ADMINISTRATION OF HPMPC AND RELATED PHOSPHONYL METHOXYALKYLCYTOSINES, issued Nov. 21, 1995 as U.S. Pat. No. 5,468,752. The subject matter of each of U.S. application Ser. Nos. 08/440,447, 08/360,995 and 08/222,128 is incorporated herein by reference thereto.

FIELD OF THE INVENTION

The invention herein relates to the compositions for and treatment of glaucoma and other conditions of abnormally increased intraocular pressure. More particularly, it relates to treatment by application of therapeutic compounds and compositions containing the compounds.

BACKGROUND OF THE INVENTION

Glaucoma

Glaucoma, which is the leading cause of blindness in the United States, is a group of diseases characterized by progressive atrophy of the optic nerve head leading to visual field loss, and, ultimately, blindness. Glaucoma is generally associated with elevated intraocular pressure, which is an important risk factor for visual field loss because it causes further damage to optic nerve fibers.

There are several types of glaucoma, including open and closed angle glaucoma, all involve the abnormal increase in intraocular pressure, primarily by obstruction of the outflow of aqueous humor from the eye, or, less frequently, by over production of aqueous humor within the eye. The most prevalent type is primary open angle glaucoma in which the aqueous humor has free access to the irridocorneal angle, but aqueous humor drainage is impaired. In contrast, in closed angle glaucoma, the irridocorneal angle is closed by the peripheral iris. The angle block can usually be corrected by surgery. Less prevalent types of glaucoma include secondary glaucomas related to inflammation, trauma and hemorrhage. Glaucoma in its various forms is widely described in the literature: see, e.g., Leibrandt, ed. (1982) *Professional Guide to Diseases*, pp. 1203–1206 and Andreoli et al., eds. (1986) Cecil: *Essentials of Medicine*, pp. 690–691.

Therapeutic treatment of glaucoma is directed at reducing intraocular pressure. Because intraocular pressure is controlled by aqueous humor dynamics, an understanding of the production and removal of aqueous humor from the eyeball provides insights into the causes of increased ocular pressure associated with glaucoma. Aqueous humor is similar in electrolyte composition to plasma, but has a lower protein content. The aqueous humor keeps the eyeball inflated, supplies the nutritional needs of the vascular lens and cornea and washes away metabolites and toxic substances within the eye. The bulk of aqueous humor formation is the product of active cellular secretion by nonpigmented epithelial cells of the ciliary process from the active transport of solute, probably sodium, followed by the osmotic flow of water from the plasma. The nonpigmented epithelial cells of the ciliary process are connected at their apical cell membranes by tight junctions. These cells and the nonfenestrated iris vessels form the blood/aqueous barrier through which blood-borne large molecules, including proteins, do not pass.

Intraocular pressure is a function of the difference between the rate at which aqueous humor enters and leaves eye. Aqueous humor enters the posterior chamber by three means: 1) active secretion by nonpigmented epithelial cells of the ciliary process; 2) ultrafiltration of blood plasma; and 3) diffusion. Newly formed aqueous humor flows from the posterial chamber around the lens and through the pupil into the anterior chamber; aqueous humor leaves the eye by passive bulk flow at the irridocorneal angle and uveoscleral outflow. Any change in 1), 2) or 3) will disturb aqueous humor dynamics and likely alter intraocular pressure.

Treatments for Glaucoma

Most treatments for glaucoma focus on reducing intraocular pressure. Treatment has involved administration of beta-blockers such as timolol to decrease aqueous humor production, epinephrine to lower intraocular pressure or diuretics such as acetazolamide to reduce aqueous production, or administration of miotic eyedrops such as pilocarpine to facilitate the outflow of aqueous humor. Acute forms of glaucoma may require peripheral iridectomy surgery to relieve pressure where drug therapy is ineffective and the patient's vision is at immediate risk. Other forms of treatment have included physical or thermal destruction ("cyclo-destruction") of the ciliary body of the eye, commonly by surgery or application of a laser beam, cryogenic fluid or high frequency ultrasound. Each of these methods of destruction is costly and unduly inversive.

There are many problems, however, in effectively treating glaucoma and with long term medicinal or surgical therapies. One problem is the difficulty in devising means to generate pharmacologically effective intraocular concentrations and to prevent extraocular side effects elicited by systemic administration. Many drugs are administered topically or locally. The amount of a drug that gets into the eye is, however, only a small percentage of the topically applied dose because the tissues of the eye are protected from such substances by numerous mechanisms, including tear turnover, blinking, conjunctival absorption into systemic circulation, and a highly selective corneal barrier.

Also, there is a risk for developing an intolerance to medical therapy or laser therapy, so that a filtration operation for control of intraocular pressure may become necessary. Present surgical techniques to lower intraocular pressure, when medication fails to decrease fluid flow into the eye or to increase fluid outflow, include procedures that permit fluid to drain from within the eye to extraocular sites by creating a fluid passageway between the anterior chamber of the eye and the potential supra-scleral/sub-Tenon's space, or, alternatively, into or through the Canal of Schlemm (see, e.g., U.S. Pat. No. 4,846,172). The most common operations for glaucoma are glaucoma filtering operations, particularly trabeculectomy. These operations involve creation of a fistula between the subconjunctival space and the anterior chamber. This fistula can be made by creating a hole at the limbus by either cutting out a portion of the limbal tissues with either a scalpel blade or by burning with a cautery through the subconjunctival space into the anterior clamber. Fluid then filters through the fistula and is either gradually absorbed by vessels within the conjunctiva or gradually filters through the conjunctival tissues to be extruded externally with the tears. In order for the surgery to be effective, the fistula must remain substantially unobstructed. These drainage or filtering procedures, however, often fail by virtue of closure of the passageway resulting from the healing of the very wound created for gaining access to the surgical site. Failures most frequently result from scarring at the site of the incisions in the conjunctiva and the tenon's capsule. The surgery fails immediately in at least 15% of patients, and long term in a much higher percentage. Presently, this consequence of trabeculectomy, closure of the passageway, is treated with 5-fluorouracil and mitomycin C, which apparently prevent closure by inhibiting cellular proliferation. These drugs, however, are highly toxic and have undesirable side effects, including scleral melting.

In view of the limited number of treatment options, there is, therefore, a need to develop more effective treatments for glaucoma. Therefore, it is an object herein to provide compositions and methods for treatment of glaucoma.

SUMMARY OF THE INVENTION

Methods for lowering intraocular pressure by administration of compositions containing effective amounts of phosphonylmethoxyalkyl nucleoside analogs are provided. One aspect of this therapy method is the apparent ability of a single dosage or a series of lower dosage intraocular injections of the administered compound to provide substantial and long lasting reduction in intraocular pressure. Relatively small reductions in pressure to reduction up to as much as 20 mm Hg or more can be obtained.

The nucleoside analogs have the formula (I):

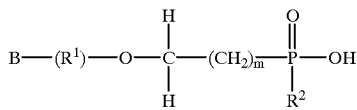

in which:

(i) $R^1$ is $CH_2(CH_2)_n$, $CH_2CH(OH)(CH_2)_n$, $CH_2CH(CH_2)_n(OH)$, $CH_2OCH(R^7)$, $CH_2OCH(R^7)(CH_2)_p$, $CH_2OCH(R^7)(CH_2)_pO$ or $O(CH_2)_pCH(R^7)O$; $R^2$ is OH; $R^7$ is H or $CH_2OH$; n is 0–6, generally 1–6, preferably 1–3, more preferably 1 or 2, and most preferably 1; p is 0–3, preferably 0 or 1; and m is 0 to about 3, preferably 0 or 1; or (ii) $R^1$, $R^2$, n, m and p are defined as in (i), and $R^1$ and $R^2$ are linked to form a cyclic ester group;

B is a pyrimidine or purine of represented by formula (II):

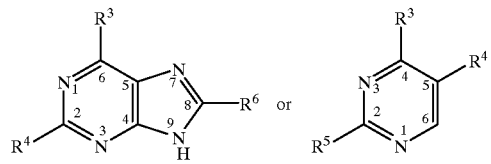

and is selected from pyrimidin-1-yl, pyrimidinyl-3-yl, purin-3-yl, purin-7-yl and purin-9-yl, or pharmaceutically acceptable salts or esters thereof. In particular, B is selected from pyrimidin-1-yl, pyrimidinyl-3-yl, purin-3-yl, purin-7-yl and purin-9-yl, or pharmaceutically acceptable salts or esters thereof, particularly, salts with alkali metals ammonia or amines, or prodrug derivatives or other derivatives thereof, particularly derivatives that penetrate the cornea when administered topically as eyedrops.

$R^3$, $R^4$, $R^5$ and $R^6$ are independently selected from $NH_2$, alkylamino, aminoalkyl, hydroxyalkyl, hydrazino, H, OH, SH, alkylthio, alkyl, alkoxy, alkoxyalkyl, halide, $CH_{3-q}(hal)_q$ in which q is 1–3 and hal is a halide, preferably, fluoro, hydroxylamino, or other group selected so that the resulting nucleoside analog retains the ability to lower intraocular pressure. Alkyl and alkoxy groups are preferably lower alkyl, preferably containing 1–3 carbons, more preferably 1–2 and most preferably are methyl groups.

$R^3$, $R^4$, $R^5$ are preferably H, $NH_2$, $CH_3$, $CH_3CH_2$, dimethylamino, halide, or OH. $R^6$ is preferably H or halide.

Preferred compounds are the phosphonylmethoxyalkyl compounds in which:

(i) $R^1$ is $(CH_2)_n$, $CH(OH)(CH_2)_n$ or $CH(CH_2)_n(OH)$, $R^2$ is OH; n is 0–6, generally 1–6, preferably 1–3, more preferably 0 or 1, and most preferably m is 0; or (ii) $R^1$ is defined as in (i), $R^2$ is —O—, and $R^1$ and $R^2$ are linked to form a cyclic ester group.

The method produces significant and long term lowering of intraocular pressure, preferably to a level that does not result in damage to the optic nerve associated with increased ocular pressure, more preferably to a pressure that is within the normal range of intraocular pressure or within a range of pressure that does not damage the optic nerve fiber or cause loss of visual field. In particular, methods for the treatment of glaucoma by administering an effective amount of impound of formula I for lowering intraocular pressure to a level that damage to optic nerve fibers and resultant visual loss does not occur are provided.

The compound of formula I is formulated, preferably as a free drug or, alternatively, encapsulated into liposomes or other long acting drug delivery systems, for administration to the aqueous humor, such as by intraocular injection, at a concentration that is effective for lowering intraocular pressure. The compounds can also be formulated for topical application to the cornea, such as in the form of eyedrops, if derivatives of the compounds are selected or designed to penetrate into the aqueous humor whereby contact with the ciliary body is effected.

The compounds are preferably formulated for single dosage administration such that amounts in the range of about 1–1000 μg, 10–200 μg, more preferably 10–50 μg and typically about 10–40 μg or 10–20 μg are delivered in a volume of about 0.05–0.150 ml, preferably 0.1 ml into the eye. Thus, compositions for the treatment of glaucoma formulated for single dosage administration that contain an effective amount, typically 10–100 μg, preferably about 10–40 μg, more preferably about 20–40 μg of a compound of formula I in a pharmaceutically acceptable carrier are provided.

The above dosages are specified with reference to (s)-1-(3-hydroxy-2-phosphonylmethoxypropyl)cytosine (HPMPC). The amount of compound will be adjusted for molecular weight differences from HPMPC so that comparable amounts on a molar basis are used. The amount is also adjusted for any difference in potency as described herein. For example, HPMPA exhibits approximately 10–50% of the potency of HPMPC. Compounds of lower potency than HPMPC, particularly those with a relatively high therapeutic index, are desirable because they permit better incremental titration of the total dosage. As discribed herein, the compounds are intended to be incrementally administered to achieve intraocular pressure that does not adversely impact on the field of vision.

The compounds may also be formulated for implantation into the anterior or posterior chamber, preferably the vitreous cavity, in sustained released formulations, such as adsorbed to biodegradable supports, including collagen sponges, or in liposomes. Sustained release formulations may be formulated for multiple dosage administration, so that during a selected period of time, such as a month or up to about a year, several dosages are administered. Thus, for example, liposomes may be prepared such that a total of about two to up to about five or more times the single dosage is administered in one injection.

In preferred embodiments, the composition is provided in a sealed sterile vial containing an amount of a compound of formula I, that upon intraocular administration will deliver 10–100 μg, preferably 10–40 μg, more preferably 10–20 μg of a compound of formula I in a volume of 0.100 ml. Typically, the vials will, thus, contain about 0.150 ml of the composition.

Also provided are kits for practice of the methods herein. The kits contain one or more containers, such as sealed vials, with sufficient composition for single dosage administration, and one or more needles, such as self sealing 25–33 gauge needles, preferably 33 gauge or smaller needles, precisely calibrated syringes or other precisely calibrated delivery device, suitable for intravitreal injection.

Administration of the composition is preferably by intraocular injection, although other modes of administration may be effective, if the sufficient amount of the compound achieves contact with the vitreous cavity. Intraocular injection may be effected by intravitreal injection, aqueous humor injection or injection into the external layers of the eye, such as subconjunctival injection or subtenon injection, or by topical application to the cornea, if a penetrating derivative of a compound is used. It is believed that a single injection or series of injections of lower dosages will be sufficient to produce prolonged, and perhaps permanent, lowering of the intraocular pressure. Typically, a relatively low dose 10 μg to about 40 μ, preferably more than about 20 μg to about 40 μg, is administered initially and intraocular pressure is monitored over a period of at least several days, typically about two or more weeks until it does not change. If the pressure is still elevated, an additional dose may be administered, and the pressure monitored as above until a sufficiently low pressure that will not cause any damage to the optic nerve fibers or result in loss of vision is achieved. In some cases, the initial series of treatments may be sufficient to achieve a permanent lowering of pressure. In other cases, additional injections may be required at infrequent intervals to sustain the lowered pressure. The amount of the compound administered may be varied by the physician to obtain the desired degree of pressure decrease. Caution should be used to avoid achieving a pressure that is lower than desired.

DETAILED DESCRIPTION AND PREFERRED EMBODIMENTS

Unless defined otherwise, all technical and scientific terms used herein have the same meaning as is commonly understood by one of skill in the art to which this invention belongs. All patents and publications referred to herein are incorporated by reference.

As used herein an effective amount of a compound for treating glaucoma is an amount that is sufficient to ameliorate, or in some manner reduce a symptom or stop progression of a condition, preferably by reducing intraocular pressure, associated with glaucoma. Such amount may be administered as a single dosage or may be administered according to a regimen, whereby it is effective. The amount may cure the glaucoma by permanently effecting a lowering of the intraocular pressure to a level that does not cause damage to the optic nerve, but, typically, is administered in order to reduce intraocular pressure, thereby ameliorating any associated pathology or symptoms of the disease. Typically, repeated administration is required to achieve the desired reduction in pressure or to halt progression of the associated pathology.

As used herein, the adverse symptoms associated with elevated intraocular pressure is/are the damage to the optic nerve observed as cupping and/or loss of visual field. Cupping refers to an observable depression in the central area or paracentral area of the optic nerve.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, the $IC_{50}$ refers to an amount, concentration or dosage of a particular compound that achieves a 50% inhibition of a maximal response, in this case reduction of intraocular pressure.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, treatment means any manner in which the symptoms or pathology of a condition, disorder or disease are ameliorated or otherwise beneficially altered. Treatment also encompasses any pharmaceutical use of the compositions herein, and particularly refers to decreases in intraocular pressure.

As used herein, amelioration of the symptoms of a particular disorder, in this instance amelioration of the progression of the physiological changes associated with glaucoma and/or reduction in intraocular pressure, by administration of a particular pharmaceutical composition refers to any lessening, whether permanent or temporary, lasting or transient that can be attributed to or associated with administration of the composition. In particular, any decrease in intraocular pressure that is sufficient to prevent, inhibit, delay or halt damage to the optic nerve as evidenced by changes in the structure of the nerve visible by ophthalmoscopy or instruments that show cupping in the optic nerve or by loss in the visual field, particularly in the periphery.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, pharmaceutical activity refers to the activity of the compounds herein to reduce intraocular pressure. For purposes herein, the activity of compounds in lowering intraocular pressure can be measured relative to the activity of HPMPC in the guinea pig model described below.

As used herein, a prodrug is a compound that, upon In vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. Prodrugs or derivatives of the compounds that permit penetration into the aqueous human when administered by topical application to the eye are of particular interest herein. By virtue of knowledge of pharmacodynamic processes and drug metabolism in vivo, once a pharmaceutically active compound is identified, those of skill in the pharmaceutical art generally can design prodrugs of the compound (see, e.g., Nogrady (1985) *Medicinal Chemistry A Biochemical Approach*, Oxford University Press, New York, pages 388–392).

As used herein, dosages of the compounds will normally be stated herein on a microgram ($\mu$g) per milliliter (ml) administered or $\mu$g/per milliliter ($\mu$g/ml) of vitreous basis. The human eye has vitreous volume of approximately 4 ml; the guinea pig vitreous volume is approximately 0.25 ml. Unless otherwise noted, typically the volume administered to a human subject is 0.1 ml, and to the guinea pig is 0.025 ml.

As used herein, lower alkyl, lower alkenyl, and lower alkynyl refer to carbon chains having six or fewer carbon atoms in a chain, preferably three or fewer. In preferred embodiments of the compounds provided herein that include alkyl, alkenyl, or alkynyl portions, the compounds include lower alkyl, lower alkenyl, and lower alkynyl portions that have three or fewer carbon atoms in a chain.

As used herein, the abbreviations for any substituent groups, protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

A. Compounds

Compositions formulated for single dosage local administration to the eye containing compounds of formula (I) and derivatives of formula (I):

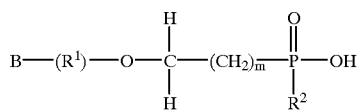

in which:

(i) $R^1$ is $CH_2(CH_2)_n$, $CH_2CH(OH)(CH_2)_n$, $CH_2CH(CH_2)_n(OH)$, $CH_2OCH(R^7)$, $CH_2OCH(R^7)(CH_2)_p$, $CH_2OCH(R^7)(CH_2)_pO$ or $O(CH_2)_pCH(R^7)O$; $R^2$ is OH or $O(CH_2)_rH$, preferably OH; $R^7$ is H or $CH_2OH$; n is 0–6, generally 1–6, preferably 1–3, more preferably 1 or 2, and most preferably 1; p is 0–3, preferably 0 or 1; r is 1–6, more preferably 1–3, most preferably 1 or 2; and m is 0 to about 3, preferably 0 or 1; or (ii) $R^1$, $R^2$, n, m and p are defined as in (i), and $R^1$ and $R^2$ are linked to form a cyclic ester group;

B is represented by the formula:

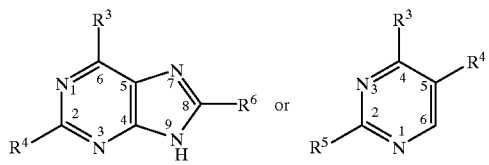

so that B is selected from pyrimidin-1-yl, pyrimidinyl-3-yl, purin-3-yl, purin-7-yl and purin-9-yl, or pharmaceutically acceptable salts or esters thereof, particularly, salts with alkali metals ammonia or amines, or other prodrug derivatives thereof, such as derivatives that penetrate the cornea to provide delivery to the aqueous cavity of the eye, are provided.

$R^3$, $R^4$, $R^5$ and $R^6$ are independently selected from $NH_2$, alkylamino, aminoalkyl, hydroxyalkyl, hydrazino, H, OH, SH, alkylthio, alkyl, alkoxy, alkoxyalkyl, halide, $CH_{3-q}(hal)_q$ in which q is 1–3 and hal is a halide, preferably fluoro, hydroxylamino, or other group selected so that the resulting nucleoside analog retains the ability to lower intraocular pressure. Alkyl and alkoxy groups are preferably lower alkyl, preferably containing 1–3 carbons, more preferably 1–2 and most preferably are methyl groups.

$R^3$, $R^4$, $R^5$ and $R^6$ are independently selected from $NH_2$, alkylamino, aminoalkyl, hydroxyalkyl, hydrazino, H, OH, SH, alkylthio, alkyl, alkoxy, alkoxy alkyl, halide, $CH_{3-q}(hal)_q$ in which q is 1–3 and hal is a halide, preferably, fluoro, hydroxylamino, or other group selected so that the resulting nucleoside analog retains the ability to lower intraocular pressure. Alkyl and alkoxy groups are preferably lower alkyl, preferably containing 1–3 carbons, more preferably 1–2 and most preferably are methyl groups.

$R^3$, $R^4$ and $R^5$ are preferably independently selected from $NH_2$, H, OH, lower alkylamino, $CH_3$, $C(hal)_3$ in which hal is halide, particularly $CF_3$ or equivalent variations thereof. $R^3$, $R^4$ and $R^5$ are more preferably H, $NH_2$, dimethylamino, halide, or OH. $R^6$ is preferably H, $CH_3$ or halide, and more preferably H or halide, paarticularly bromo. $R^3$, $R^4$, $R^5$ and $R^6$ can be selected so that B is uridinyl, thymidinyl, cytosinyl, or adeninyl or derivatives thereof.

In more preferred embodiments the compounds are those in which $R^1$ and $R^2$ are (i) only, in which $R^1$ is $CH_2CH(OH)(CH_2)_n$, $CH_2CH(CH_2)_n(OH)$, $CH_2OCH(R^7)$, $CH_2OCH(R^7)(CH_2)_p$, $CH_2OCH(R^7)(CH_2)_pO$ or $O(CH_2)_pCH(R^7)O$; $R^2$ is OH or $O(CH_2)_rH$; $R^7$ is OH or $(CH_2)_rOH$, preferably $(CH_2)OH$; n is 0–6, preferably 0–3; r is 1–6, preferably 1–3, more preferably 1; p is 0–3; and m is 0 to 3.

Most of the compounds will have an asymmetric carbon atom, such as when n is 1 and $R^1$ is other than methylene, and will exist in more than one enantiomeric form. In such instances, the preferred compounds are racemic mixtures (RS) or, preferably, are in the (S) form, and are in the form of a free acid or salt thereof. Compounds of formula (I) that contain a chiral center are preferred, and it is preferred that it is in the s configuration. Racemic mixtures are, however, acceptable.

Of the compounds of formula (I), those with the following formulae are of particular interest:

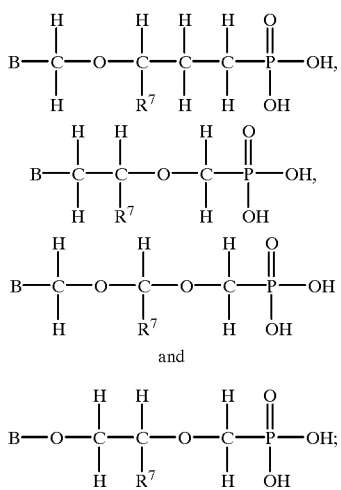

in which B, $R^7$ and preferred embodiments of B, are defined as above.

Among other preferred compounds of formula (I) are those of formula (II):

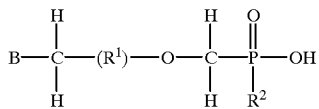

in which:
(i) $R^1$ is $(CH_2)_n$,

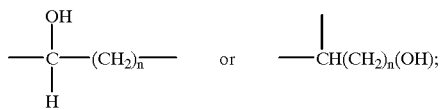

$R^2$ is OH; and
n is 0–6, generally 1–6, preferably 1–3, more preferably 1 or 2, and most preferably 1; or
(ii) $R^1$ and $R^2$, which are as defined in (i), are linked to form a cyclic ester group;
in which B and preferred embodiments of B, are as defined above.

The compounds of formulae (I) and (II) for use in the methods herein include, but are not limited to, compounds in which B is selected from uracil-1-yl, cytosin-1-yl, 5-methylcytosin-1-yl, thymin-1-yl, 5-fluorouracil-1-yl, uracil-3-yl, cytosin-3-yl, 5-methylcytosin-3-yl, thymin-3-yl, 5-fluorouracil-3-yl, guanin-9-yl, guanin-7-yl, guanin-3-yl, adenin-9-yl, adenin-7-yl, adenin-3-yl, hypoxanthin-9-yl, hypoxanthin-7-yl, hypoxanthin-3-yl, 2-methyladenin-9-yl, 2-methyladenin-7-yl, 2-methyladenin-3-yl, 2-methylthioadenin-9-yl, 2-methylthioadenin-7-yl, 2-methylthioadenin-3-yl, 2-aminoadenin-9-yl, 2-aminoadenin-7-yl, 2-amino-adenin-3-yl, 2-aminopurin-9-yl, 2-aminopurin-7-yl, 2-aminopurin-3-yl, $N^6$-dimethyladenin-9-yl, $N^6$-dimethyladenin-7-yl, $N^6$-dimethyladenin-3-yl, 8-bromoadenin-9-yl, 8-bromoadenin-7-yl, 8-bromoadenin-3-yl, 8-hydroxyadenin-9-yl, 8-hydroxyadenin-7-yl, 8-hydroxyadenin-3-yl, 6-hydroxylaminopurin-9-yl, 6-hydroxylaminopurin-7-yl, 6-hydroxylaminopurin-3-yl, 6-hydrazinopurin-9-yl, 6-hydrazinopurin-7-yl, 6-hydrazinopurin-3-yl, 6-thiopurin-9-yl, 6-thiopurin-7-yl, 6-thiopurin-3-yl, purin-9-yl, purin-7-yl, purin-3-yl, xanthin-9-yl, xanthin-7-yl, and xanthin-3-yl.

Preferred among these compounds are those in which B is uracil-1-yl, cytosin-1-yl, 5-methylcytosin-1-yl, thymin-1-yl, 5-fluorouracil-1-yl, guanin-9-yl, guanin-7-yl, adenin-3-yl, hypoxanthin-9-yl, 2-methyladenin-9-yl, 2-methylthioadenin-9-yl, 2-aminoadenin-9-yl, 2-aminopurin-9-yl, $N^6$-dimethyladenin-9-yl, 8-bromoadenin-9-yl, 8-hydroxyadenin-9-yl, 6-hydroxylaminopurin-9-yl, 6-hydrazinopurin-9-yl, 6-thiopurin-9-yl, purin-9-yl, and xanthin-9-yl. Compounds in which B is cytosin-1-yl, uracil-1-yl, 5-methylcytosin-1-yl, thymin-1-yl, and 5-fluorouracil-1-yl may be more preferred.

Other preferred compounds include, but are not limited to, the N-(2-phosphonylmethoxyethyl) [PME] and N-(3-hydroxy-2-phosphonylmethoxypropyl) [HPMP] pyrimidine and purine nucleoside analogs, particularly the pyrimidine analogs. HPMP analogs are presently generally preferred and sHPMP analogs are presently more preferred.

In preferred compounds $R^1$ is a chiral center and is preferably in the s configuration. Some particularly preferred compounds include, but are not limited to: 9-(s)-(2-phosphonylmethoxy-3-hydroxy-propyl)adenine [HPMPA], 9-(2-phosphonylmethoxyethyl)adenine [PMEA], (s)-1-(3-hydroxy-2-phosphonylmethoxypropyl)cytosine [HPMPC], (2-phosphonylmethoxyethyl)cytosine [PMEC], (2-phosphonylmethoxyethyl)guanine [PMEG], 1-(s)-3-hydroxy-2-phosphonylmethoxypropyluracil [(S)-HPMPU], 9-(s)-3-hydroxy-2-phosphonylmethoxypropylguanine [(S)-HPMPG], (2-phosphonylmethoxyethyl)-2,6-diaminopurine [PMEDAP], and 9-(s)-2-phosphonylmethoxypropyladenine [(S)-PMPA].

The compounds cyclic (s)-3-hydroxy-2-phosphonylmethoxypropylcytosine [cHPMPC] and 9-(cyclic(s)-3-hydroxy-2-phosphonylmethoxypropyl)adenine [cHPMPA], are also among the preferred compounds. The compounds 9-(r)-3-hydroxy-2-phosphonylmethoxypropyladenine [(R)-HPMPA], 9-(r)-2-phosphonylmethoxypropyladenine [(R)-PMPA] and 9-(2-phosphonylmethoxyethyl)adenine [PMEA] are also intended for use herein.

Among preferred compounds herein are: 9-(s)-(2-phosphonylmethoxy-3-hydroxy-propyl)adenine [HPMPA] and (s)-1-(3-hydroxy-2-phosphonylmethoxypropyl) cytosine [HPMPC].

B. Preparation and selection of compounds

1. Preparation

Some of the compounds provided herein are compounds that are available for use as antiviral agents [see, e.g., U.S. Pat. Nos. 5,142,051 and 4,724,233; see, also U.S. Pat. Nos. 4,605,658, and 4,230,708 and De Clercq et al. (1991) *Biochemical Pharmacology* 42:963–972] and, thus, may be obtained from commercial sources or synthesized by known methods [see, e.g., U.S. Pat. Nos. 5,142,051 and 4,724,233]. Novel compounds of formulae (I) and (II) may be prepared by modification of the procedures for preparation of the known compounds. Such modification is within the level of skill of the art of synthetic organic chemistry.

Use of and formulation of the compounds for lowering intraocular pressure has not heretofore been described. Antivirally effective dosages, if administered to the eye, would necessarily be lower than dosages for lowering intraocular pressure in order to avoid permanently reducing intraocular pressure in subjects that do no have elevated intraocular pressure or glaucoma.

2. Selection of compounds

The compounds of formulae (I) and (II) can be selected on the basis of their activity in the guinea pig model. For example, injection of HPMPC, cHPMPC or HPMPA into the vitreous cavity of the guinea pig eye, results in a decrease intraocular pressure that parallels decreases in human eyes. The results appear to be directly extrapolatable to effective dosages in humans. Normal intraocular pressure in the guinea pig, which is very similar to humans, is a median of 14.7 mm Hg, and the normal range is between about 10 mm to about 22 mm. Among these compounds HPMPC causes the largest drop in IOP/$\mu$g administered; and cHPMPC causes the least drop. All compounds that show activity in this model, however, should be useful, since it is desirable for treatment to be effected by administering a series of administrations of the compound in order to avoid lowering IOP too much.

Histologic studies of the guinea pigs show changes in the structure of the ciliary body that would be expected to lower aqueous secretion. Optical properties of the compound when injected into the vitreous cavity were assessed by indirect ophthalmoscopy and fundus photography, as well as by observing the behavioral characteristics of the animals who underwent intravitreal injection. In all cases, the optical pathways were normal, as was animal visual behavior, indicating that the compound does not obstruct or affect the visual pathways in any way. This indicates that the intravitreal injection of the compound as described should result in no adverse effects and will have a major therapeutic effect.

In the guinea pig model, injections are performed with anesthetized animals and baseline intraocular pressures are taken for comparison with post injection pressures. Manometric measure of intraocular pressure are performed by placing a 33 gauge cannula into the anterior of the guinea pig eye and determining the pressure by manometry using a pressure transducer and recording apparatus. Injection, via the limbus, of 0.05 ml compositions containing 2 $\mu$g, 10 $\mu$g, 50 $\mu$g, 80 $\mu$g, 100 $\mu$g and 250 $\mu$g of HPMPC (per 0.25 ml vitreous) resulted in decreases in pressure, indicative of a dose-response relationship in the range of about 10–200 $\mu$g/0.25 ml vitreous in this model. The results were parallel, though higher in concentrations, to results observed in humans in which the dose response curve is linear in the range of about 10 $\mu$g up to about 80–100 $\mu$g injected per 4 ml of vitreous in the human eye. Multiple doses of HPMPC in the this model also showed a clear dose response.

Injection of 250 $\mu$g HPMPC (about 1 mg/ml vitreous) in this model results in a substantial drop in intraocular pressure that ultimately reached zero within several days. The effect appears to be approximately equivalent to administration of about 100 $\mu$g (25 $\mu$g/ml vitreous) to a human eye. A 50 $\mu$g (200 $\mu$g/cc) injection to guinea pig lowers the pressure by approximately 30–60% (to lower than 10 mm Hg) without adverse effects. This is equivalent to about 20–40 $\mu$g injected into the human eye. A dose of HPMPC of 6.25 $\mu$g caused minimal to no drop in IOP; and a dose of 156 $\mu$g causes a similar, slightly increased, drop in IOP. Administration of 500 $\mu$g resulted in an IOP of zero.

In humans, administration of 10–20 $\mu$g of HPMPC causes a drop of about 2–4 mm Hg, and repeated injections every six weeks causes further lowering of IOP. At doses of 40 $\mu$g, there is a larger drop, and at 100 $\mu$g the IOP drops to zero.

Injection of cHPMPC at dose equivalents to HPMPC of 500 $\mu$g lowered IOP gradually from the normal range to between 2 and 6 mm Hg over the course of 4 weeks. Doses of 156 $\mu$g (HPMPC equivalent) had no effect. This indicates that cHPMPC is a very mild pressure lowering agent, and, thus, will permit gradual lowering of IOP to the normal range at a useful dosage range (dosages in the range of 100 $\mu$g to 400 $\mu$g).

HPMPA, which has also been tested in this model, appears to be about 10 to 50% less potent than HPMPC, and appears have a higher therapeutic index dose (therapeutic index=dosage required reduce the pressure zero/dosage to drop to 10%) than HPMPC. HPMPA, will, thus, also be suitable for therapeutic use for treating glaucoma, since it will permit precise titration of the appropriate total dosage to achieve the desired decrease in pressure.

Other compounds of formulae (I) and (II) are assessed for intraocular pressure lowering activity in this model. Compounds that exhibit intraocular pressure lowering activity substantially similar to HPMPC or with greater specific activity than HPMPC in this model are preferred for use herein. Compounds that are less potent, but exhibit specific activity that is approximately at least about 30–50% of HPMPC are also suitable for use. As long as the activity is sufficient for a therapeutically effective dose (equivalent in activity to about 10 $\mu$g of HPMPC) to be delivered to a human eye in about 0.100 ml, a selected compound is suitable for use herein. Thus, any compound that exhibits detectable IOP-lowering activity in this model should be suitable for use herein.

C. Formulation

Compositions containing therapeutically effective for lowering intraocular pressure amounts of the compounds of formula (I) are provided herein. The compounds are formulated in concentrations suitable for single dosage administration by intraocular administration in an amount that incrementally lowers intraocular pressure from an elevated level to a level that is sufficiently low to avoid the damaging effects of elevated intraocular pressure. Typically the concentrations of compounds are between about 10% and 50%, preferably greater than about 20% and up to about 40% weight/volume. The compositions are preferably formulated for intraocular, preferably intravitreal administration, such that injection of about 0.100 ml delivers about 10 $\mu$g to less than about 100 $\mu$g, preferably about 10 $\mu$g to about 40 $\mu$g or 50 $\mu$g. Presently, compositions formulated for single dosage administration of about 40 $\mu$g in a volume of 0.1 ml are preferred.

To prepare compositions, one or more compounds of formula (I) or (II) are mixed with a suitable ophthalmologically acceptable carrier. Upon mixing or addition of the compound(s), the resulting mixture may be a solution, suspension, emulsion or the like. In addition, the compounds may be formulated as the sole pharmaceutically active ingredient in the composition or may be combined with other active ingredients, particularly anti-glaucoma agents, or pharmaceutically inactive ingredients.

Of the compounds of formulae (I) and (II), those that are polar and highly water soluble are well suited to ocular use, especially where intraocular injection is the preferred method of administration. If necessary, however, pharmaceutically acceptable salts or other derivatives of the conjugates may be prepared. If the resultant mixture is amenable to filtration, it can be filter sterilized using nylon 66 matrix 0.22 μm sterile syringe filter systems that cause no ocular toxicity.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems, particularly the guinea pig model described herein. Based upon a comparison of the activity of a particular compound in this model with compounds, such as HPMPC, that are exemplified herein, compositions containing effective amounts of the selected compound are prepared. Typically, a therapeutically effective dosage, upon single dosage administration, should reduce intraocular pressure by an amount less than 20 mm Hg, preferably less than 10 mm Hg, and on the order of a 10%–30% decrease, depending upon the initial pressure. This may be repeated, typically after an interval of at least 14 days or more, until intraocular pressure is sufficiently reduced to a level at which the optic nerve damage and visual field loss is halted or the rate of damage or loss reduced, preferably substantially reduced.

The compositions are formulated in an ophthalmologically acceptable carrier for intraocular, preferably intravitreal, administration in a volume of between about 0.05 ml and 0.150 ml, preferably about 0.05 and 0.100 ml, containing between about 1–1000 μg, preferably, 10 μg to less than about 100 μg, more preferably about 10–50 μg, and more preferably about 20–40 μg of a compound of formula (I) or (II). Thus, the compositions contain between about 10% and 50% (weight/volume), with about 25% or 30% to 40–50% preferred, of a compound of formula (I) or (II).

For administration by intraocular injection or via eyedrops, suitable carriers include, but are not limited to, physiological saline, phosphate buffered saline (PBS), balanced salt solution (BSS), lactate Ringers solution, and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art. Suitable ophthalmologically acceptable carriers are known. Solutions or mixtures intended for ophthalmic use may be formulated as 0.01%–10% isotonic solutions, pH about 5–7, with appropriate salts [see, e.g., U.S. Pat. No. 5,116,868, which describes typical compositions of ophthalmic irrigation solutions and solutions for local application]. Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The compounds of formulae (I) and (II) may be prepared with carriers that protect them against rapid elimination from the body, such as time release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and other types of implants that may be placed directly into the anterior or posterior chamber or vitreous cavity of the eye. The compositions may also be administered in pellets, such as Elvax pellets (ethylene-vinyl acetate copolymer resin).

Liposomal suspensions, including tissue-targeted liposomes, may also be suitable as pharmaceutically acceptable carriers. For example, liposome formulations may be prepared by methods known to those of skill in the art [see, e.g., Kimm et al. (1983) Bioch. Bioph. Acta 728:339–398; Assil et al. (1987) Arch Ophthalmol. 105:400; and U.S. Pat. No. 4,522,811]. The nucleoside analogs provided herein may be encapsulated into the aqueous phase of liposome systems. HPMPC has been encapsulated into liposomes using a modification of the method of Kimm et al. and described in EXAMPLE 4.

The active materials can also be mixed with other active materials, that do not impair the desired action, or with materials that supplement the desired action or have other action, including viscoelastic materials, such as hyaluronic acid, which is sold under the trademark HEALON, which is a solution of a high molecular weight (MW) of about 3 millions fraction of sodium hyaluronate [manufactured by Pharmacia, Inc; see, e.g., U.S. Pat. Nos. 5,292,362, 5,282, 851, 5,273,056, 5,229,127, 4,517,295 and 4,328,803], VISCOAT [fluorine-containing (meth)acrylates, such as, 1H,1H, 2H,2H-heptadecafluorodecylmethacrylate; see, e.g., U.S. Pat. Nos. 5,278,126, 5,273,751 and 5,214,080; commercially available from Alcon Surgical, Inc.], ORCOLON [see, e.g., U.S. Pat. No. 5,273,056; commercially available from Optical Radiation Corporation], methylcellulose, methyl hyaluronate, polyacrylamide and polymethacrylamide [see, e.g., U.S. Pat. No. 5,273,751]. The viscoelastic materials are present generally in amounts ranging from about 0.5 to 5.0%, preferably 1 to 3% by weight of the conjugate material and serve to coat and protect the treated tissues. The compositions may also include a dye, such as methylene blue or other inert dye, so that the composition can be seen when injected into the eye. Additional anti-glaucoma or intravitreal pressure-lowering agents, including beta-blockers, such as epinephrine, and diuretics such as acetazolamide, or pilocarpine, also may be included.

The compositions can be enclosed in ampules, disposable syringes or multiple or single dose vials made of glass, plastic or other suitable material. Such enclosed compositions can be provided in kits. In particular, kits containing vials, ampules or other container, preferably disposable vials with sufficient amount of the composition to deliver about 0.100 ml thereof, and disposable needles, preferably self sealing 25–30 gauge needles, are provided herein. Prepackaged vials of compositions, containing concentrations of compounds of about 10 μg/0.100 ml, 20 μg/0.100 ml, 25 μg/0.100 ml, 30 μg/0.100 ml, 35 μg/0.100 ml p to about 100 μg/0.100 ml in 5 or 10 μg/0.100 ml increments, with sufficient volume, typically 0.125–0.150 ml, although greater volumes, 1, 5 and 10 ml or higher may be packaged, to deliver 0.100 ml are provided. For treatment of elevated intraocular pressure compositions in the range greater than about 20 μg/0.100 ml and less than about 80 μg/0.100 ml, preferably, about 40 μg/0.100 ml are preferred.

Finally, the compounds may be packaged as articles of manufacture containing packaging material, typically a vial, an ophthalmologically acceptable composition containing a compound of formula (I) or (II) provided herein, which is effective for lowering intraocular pressure, and a label that indicates that the compound or salt thereof is used for lowering intraocular pressure.

D. Administration

The compositions containing the compounds are administered intraocularly or by other means, such as topically in the form of penetrating eyedrops, whereby contact of the compounds with the aqueous humor is effected. Intraocular administration may be effected by intravitreal injection, aqueous humor injection, injection into the external layers of the eye, such as subconjunctival injection or subtenon injection, preferably in free form, but, alternatively, in liposomes or other sustained drug delivery device. Administration of the compound is preferably by intravitreal injection, preferably through self sealing 25–30 gauge needles or other suitably calibrated delivery device. Injection into the eye may be through the pars plana via the self-sealing needle.

Without being bound by any theory regarding the mechanism of this extended or possibly permanent period of efficacy for the treatment of glaucoma contact of the compounds provided herein with the ciliary body decreases the ability of the ciliary body of the eye to secrete aqueous humor. Since the ciliary body is preferably accessed by intravitreal injection or by aqueous humor injection, such modes of administration are presently preferred. Administration by other modes that ultimately result in decreased intraocular pressure, such as injection into the external layers of the eye, such as subconjunctival injection or subtenon injection, or topical application to the cornea in a form that penetrates into the eye, can be employed. Such modes of administration should be designed to result in introduction of a compound within the aqueous or vitreous fluids, thereby providing access to the ciliary body.

The routes of administration, especially by injection, are specialized and unique and the properties of the compound that render it highly suitable for this use include its lack of toxicity (other than to decrease aqueous secretion), high intraocular therapeutic index, optical clarity, which precludes it from adversely affecting the vision of the eye to which it is administered, and its high water solubility which allows extremely small volumes to be injected under topical or local anesthetics into the mid-vitreous cavity of the human eye.

Typically, in order to avoid excessive lowering of intraocular pressure, the compounds are administered in incremental dosages, generally more than about 20 $\mu$g up to about 40 or 50 $\mu$g/injection, depending upon the starting pressure and observed optic nerve fiber and visual field changes. The dosage should be selected based upon the initial starting pressure and observed symptoms, and carefully selected to achieve a resulting pressure that is within normal range of 8–22 mm Hg. It appears that in many cases, a single intravitreal injection may be sufficient to obtain permanent reduction. Care should, however, be taken to avoid achieving too large a reduction in pressure. Consequently, incremental doses may be preferred.

After administration of a single injection, intraocular pressure is monitored for one to three weeks, and, if necessary, a second dose of the composition is administered, followed by one to three weeks of monitoring. This is repeated until the desired, generally, although not necessarily within the range of 8–22 mm Hg, intraocular pressure is attained. It is understood that there are variations in the range of normal pressure. Consequently, for glaucoma patients, elevated pressure is determined by the pressure and evidence of optic nerve damage as evidenced visually, by a decrease in the visual field or other test indicative of such damage.

In glaucoma patients, intraocular pressures are typically above 18–20 mm Hg, but in some patients, the loss of visual field and optic nerve changes are observed at pressures in the range of 15–22 mm Hg. Such glaucoma is referred to as low tension glaucoma. Also, in some patients, the changes in visual field and the optic nerve do not occur until the pressure is as high as 30–33 mm Hg. In either case, the treatment is designed to effect a lowering of intraocular pressure, whereby the adverse symptoms are halted or their progress slowed. Effectiveness of treatment can be assessed by observing a decrease in pressure, whatever the pressure was before treatment, and a concomitant halting or slowing of damage to the optic nerve and visual field loss.

Thus, the absolute amount of pressure change, and ultimately, number of doses and dosage of the compounds herein, must be determined with reference to each patient. Desirably, the lowest total dosage that effects treatment, as defined herein, should be administered. Therefore, small incremental doses, typically about 20–60 $\mu$g, preferably 20–40 $\mu$g or about 50 $\mu$g per injection (0.100 ml injected), depending upon the intraocular pressure and observed changes in the optic nerve and visual field loss, are administered. Lower dosages, as low as about 10 $\mu$g, 20 $\mu$g or 30 $\mu$g, may be administered when the initial pressure is within, or close to, normal range. Presently, dosages on the order of about 40 $\mu$g (35–45 $\mu$g) per injection appear to be preferred. The volume injected may vary between about 0.05–0.15 ml.

The patient is thereafter periodically monitored, and, if intraocular pressure increased, additional dose(s) is (are) administered. Where the reduction in pressure is not permanent, it is expected that further injections will be required only on an infrequent basis, since the intraocular pressure lowering effects of these compounds are long term and possibly permanent.

It is further understood that, for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed methods or concentrations of active compounds in the claimed compositions. It is also understood that the concentrations of the compounds are specified in weight/volume with reference to HPMPC and that the compounds of formula (I) or (II) vary in molecular weight and potency compared to HPMPC. Adjustments in amounts for molecular weight differences and potency differences from HPMPC are intended to be encompassed herein. Thus, if a compound exhibits 50% of the activity of HPMPC in the guinea pig model set forth herein, it is understood that the range of concentrations, expressed as $\mu$g, will be approximately twice the ranges set forth for HPMPC. Also, if the molecular weight differs by about 2% or more, the concentrations will be corrected accordingly.

The following examples are included for illustrative purposes only and are not intended to limit the scope of the invention.

EXAMPLE 1

Intravitreal injection of 10 $\mu$g–100 $\mu$g HPMPC

Twenty subjects having relatively normal or reduced intraocular pressure, but suffering from cytomegalovirus (CMV) retinitis associated with HIV infection, were injected into the vitreous cavity with HPMPC in an amount of 10–100 $\mu$g in total volume of 0.1 ml. It is noted that individuals infected with HIV that have AIDS exhibit reduced intraocular pressure; thus, the absolute values of the pressures observed in these subjects must be viewed in this context.

The pressure lowering effect began within 3–14 days and was observed to be long lasting. The degree of pressure reduction was a function of the dosage, with the lowest dosages (~10 μg/ml) producing relatively small amounts of pressure reduction, the largest (~100 μg/ml) producing the maximum reduction (in some cases down to essentially 0 mm Hg), and the intermediate dosages producing intermediate degrees of pressure reduction.

EXAMPLE 2

Intravitreal injection of 20 μg HPMPC

The effects of injection of 0.100 ml (sterile saline) containing of 20 μg HPMPC in a consecutive series of 38 eyes of AIDS patients infected with CMV were assessed. Intraocular pressure was measured by applanation tonometry at baseline, weeks 2 and weeks 4–6 after each injection. The analysis was performed on a series of 95 injections and pairs of means were compared utilizing the Tukey-Kramer technique [JMP software, SAS Institute, Carey, N.C.], which corrects for multiple comparisons.

Twenty-six patients (52 eyes) were studied at baseline, 38 eyes received 1 injection, 16 eyes received 2 injections, and 7 eyes received 3 injections. The mean intraocular pressure at baseline was 9.82; two weeks after the first injection it was 7.31, and at 4–6 weeks, it was 8.29. Two weeks after the second injection, the mean intraocular pressure was 6, and after 4–6 weeks it was 7.25. Two weeks after the third injection, mean intraocular pressure was 7.14, and after 4–6 weeks it was 8. Tukey-Kramer HSD analysis [JMP software, SAS Institute, Carey, N.C.], revealed that the difference between baseline pressure and pressure two weeks after the first injection, the difference between baseline and the pressure two weeks after the second injection, and the difference between baseline and the pressure at the 4–6 weeks after the second injection were statistically significant.

EXAMPLE 3

Effect of 40 μg intravitreal injection of HPMPC on intraocular pressure

HPMPC (40 μg in 0.100 ml) was injected into test subjects who were CMV-infected AIDS patients. Three eyes of three patients have been injected with 40 μg of HPMPC. All eyes had initial pressures in the low normal range typical of AIDS patients. In one eye, the initial pressure was 14; it was 12 on day 7 and 9 on days 35 and 31. In the second eye in the second patient, the initial pressure was 10 and was 3 on day 11 and 2 on day 46. The pressure in the treated eye of the third patient was initially 10. After injection, it was 4 on day 11, and 5 on day 24; vision remained good.

These results, as well as those in Examples 1 and 2, indicate that the drop in intraocular pressure is long in duration and may be permanent. Further, comparisons of the results achieved with 40 μg injections compared to 20 μg, 10 μg, and 100 μg injections indicate that there is a dose related effect on intraocular pressure.

EXAMPLE 4

Preparation of liposome encapsulated HPMPC

A chloroform lipid mixture was prepared by dissolving dimyristoyl glycerol (1.5 mg), triolein (1.68 mg) and cholesterol (5.81 mg) dissolved in 1 ml of chloroform in a vial. HPMPC (1 mg/ml sucrose solution) was dissolved in 200 mmol sucrose, pH 6.8. One ml of this solution was added dropwise to a vial containing the chloroform lipid mixture. The vial was tightly sealed and vortexed for 6 min to produce spherules of HPMPC droplets coated with a lipid monolayer floating in a pool of chloroform and excess lipids. One ml of this mixture was added rapidly to each of two vials containing 2.5 ml glucose (240 mmol/liter), and the suspension was vortexed for four seconds. The resulting liposomes were then dried by passing nitrogen over them (8 liters per minute) in a flask containing 250 mmol per liter of sucrose until no detectable chloroform remained. The mixture was centrifuged at 400×G for 10 min, the supernatant was removed and the pellet of liposomes was resuspended in 0.9% sodium chloride solution and recentrifuged. This wash step was repeated 5 times in order to remove any unencapsulated HPMPC.

Drug release studies were performed in triplicate at 37° C. as follows. The liposomes were suspended in phosphate buffered saline in a 30 ml syringe mounted on a revolving rotor. At designated time intervals, 3 ml aliquots were removed and centrifuged. The resulting supernatants were withdrawn, the pelleted liposomes were disrupted by freezing and resuspending in 1 ml distilled water and the concentration of HPMPC determined by HPLC and/or ultraviolet absorption at 254 nm. Spectrophotometric analyses were performed by diluting the samples with chloroform-methanol (2:3 v/v) and the concentration determined by comparison with a standard curve.

The liposomes are injected in the same manner that free drug is injected, except that a slightly larger gauge needle (25–27 gauge) may be needed, and the HPMPC is slowly released from the liposomes over weeks to months, thereby providing gradual decrease in pressure and possibly, if higher dosages are administered, avoiding the need for additional injections. The efficacy period of the encapsulated HPMPC appears to be between about 170 and 240 days.

Since modifications will be apparent to those of skill in this art, it is intended that this invention be limited only by the scope of the appended claims.

What is claimed is:

1. A method for reducing intraocular pressure, comprising administering to the eye an effective amount of a compound of formula I:

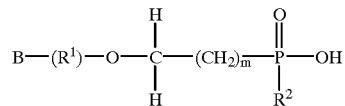

or a pharmaceutically acceptable salt or ester thereof, wherein:

$R^1$ and $R^2$ are (i) or (ii) as follows:

(i) $R^1$ is $CH_2CH(OH)(CH_2)_n$, $CH_2CH(CH_2)_n(OH)$, $CH_2OCH(R^7)$,
$CH_2OCH(R^7)(CH_2)_p$, $CH_2OCH(R^7)(CH_2)_pO$ or $O(CH_2)_pCH(R^7)O$;

$R^2$ is OH or $O(CH_2)_rH$;

$R^7$ is OH or $(CH_2)_rOH$;

n is 0–6;

r is 1–6;

p is 0–3; and m is 0 to 3

(ii) $R^1$, $R^2$, n, m, r and p are defined as in (i), and $R^1$ and $R^2$ are linked to form a cyclic ester group;

B is a pyrimidine or purine of formula (II):

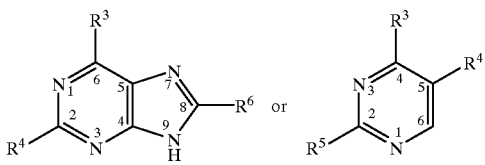

and is selected from the group consisting of pyrimidin-1-yl, pyrimidinyl-3-yl, purin-3-yl, purin-7-yl and purin9-yl; and $R^3$, $R^4$, $R^5$ and $R^6$ are independently selected from $NH_2$, alkylamino, aminoalkyl, hydroxyalkyl, hydrazino, H, OH, SH, alkylthio, alkyl, alkoxy, alkoxyalkyl, halide, hydroxylamino and $CH_3q(hal)q$ in which q is 1–3 and hal is a halide; and the amount is effective for lowering intraocular pressure.

2. A method for reducing intraocular pressure, comprising administering to the eye an effective amount of a compound selected from the group consisting of:

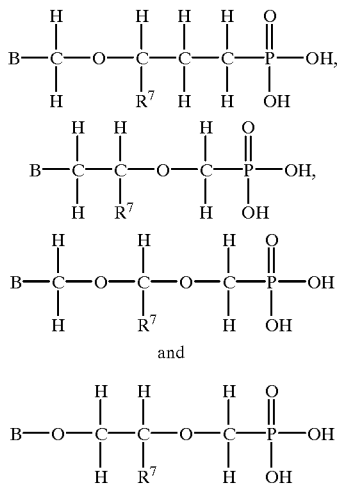

or a pharmaceutically acceptable salt or ester thereof, wherein:

$R^7$ is H, OH, or $(CH_2)_rOH$; and

B is a pyrimidine or purine of formula (II);

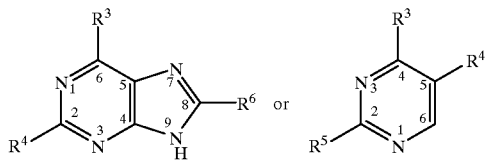

and is selected from the group consisting of pyrimidin-1-yl, pyrimidinyl-3-yl, purin-3-yl, purin-7-yl and purin-9-yl;

$R^3$, $R^4$, $R^5$ and $R^6$ are independently selected from $NH_2$, alkylamino, aminoalkyl, hydroxyalkyl, hydrazino, H, OH, SH, alkylthio, alkyl, alkoxy, alkoxyalkyl, halide, hydroxylamino and $CH_{3-q}(hal)_q$ in which q is 1–3 and hal is a halide; and the amount is effective for lowering intraocular pressure.

3. The method of claim 1, wherein:

$R^1$ is $CH_2CH(OH)(CH_2)_n$, $CH_2CH(CH_2)_n(OH)$, $CH_2OCH(R^7)$, $CH_2OCH(R^7)(CH_2)_p$, $CH_2OCH(R^7)(CH_2)_pO$ or $O(CH_2)_pCH(R^7)O$;

$R^2$ is OH or $O(CH_2)_rH$;
$R^7$ is OH or $(CH_2)_rOH$;
n is 0–6;
r is 1–6;
p is 0–3; and
m is 0 to 3.

4. The method of claim 1, wherein the compound has formula (III):

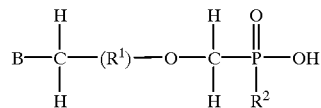

wherein $R^1$ and $R^2$ are selected from (i) or (ii):

(i) $R^1$ is $—(CH_2)_n—$,

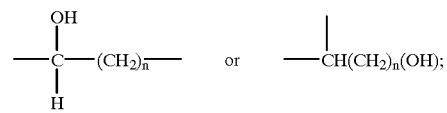

and $R^2$ is OH; or (ii) $R^1$ and $R^2$, which are as defined in (i), are linked to form a cyclic ester group.

5. The method of claim 1, wherein n is 1–3, p is 0 or 1, r is 1 and m is 0 or 1.

6. The method of claim 1, wherein $R^3$, $R^4$ and $R^5$ are each independently selected from H, $NH_2$, $CH_3$, $CH_3CH_2$, $CF_3$, dimethylamino, halide, and OH; and $R^6$ is H or halide.

7. The method of claim 1, wherein B is selected from among uracil-1-yl, cytosin-1-yl, 5-methylcytosin-1-yl, thymin-1-yl, 5-fluorouracil-1-yl, uracil-3-yl, cytosin-3-yl, 5-methylcytosin-3-yl, thymin-3-yl, 5-fluorouracil-3-yl, guanin-9-yl, guanin-7-yl, guanin-3-yl, adenin-9-yl, adenin-7-yl, adenin-3-yl, hypoxanthin-9-yl, hypoxanthin-7-yl, hypoxanthin-3-yl, 2-methyladenin-9-yl, 2-methyladenin-7-yl, 2-methyladenin-3-yl, 2-methylthioadenin-9-yl, 2-methylthioadenin-7-yl, 2-methylthioaldenin-3-yl, 2-aminoadenin-9-yl, 2-aminoadenin-7-yl, 2-amino-adenin-3-yl, 2-aminopurin-9-yl, 2-aminopurin-7-yl, 2-aminopurin-3-yl, $N^6$-dimethyladenin-9-yl, $N^6$-dimethyladenin-7-yl, $N^6$-dimethyladenin-3-yl, 8-bromoadenin-9-yl, 8-bromoadenin-7-yl, 8-bromoadenin-3-yl, 8-hydroxyadenin-9-yl, 8-hydroxyadenin-7-yl, 8-hydroxyadenin-3-yl, 6-hydroxylaminopurin-9-yl, 6-hydroxylaminopurin-7-yl, 6-hydroxylaminopurin-3-yl, 6-hydrazinopurin-9-yl, 6-hydrazinopurin-7-yl, 6-hydrazinopurin-3-yl, 6-thiopurin-9-yl, 6-thiopurin-7-yl, 6-thiopurin-3-yl, purin-9-yl, purin-7-yl, purin-3-yl, xanthin-9-yl, xanthin-7-yl, and xanthin-3-yl.

8. The method of claim 7, wherein B is selected from the group consisting of uracil-1-yl, cytosin-1-yl, 5-methylcytosin-1- yl, thymin-1-yl, 5-fluorouracil-1-yl, guanin-9-yl, guanin-7-yl, adenin-3-yl, hypoxanthin-9-yl, 2-methyladenin-9-yl, 2-methylthioadenin-9-yl, 2-aminoadenin-9-yl, 2-aminopurin-9-yl, $N^6$-dimethyladenin-9-yl, 8-bromoadenin-9-yl, 8-hydroxyadenin-9-yl, 6-hydroxylaminopurin-9-yl, 6-hydrazinopurin-9-yl, 6-thiopurin-9-yl, purin-9-yl, and xanthin-9-yl.

9. The method of claim 7, wherein B is selected from- the group consisting of adenin-9-yl, cytosin-1-yl, uracil-1-yl, 5-methylcytosin-1-yl, thymin-1-yl, and 5-fluorouracil-1-yl.

10. The method of claim 1, wherein the compound is selected from among 9-(s)-(2-phosphonylmethoxy-3- hydroxy-propyl)adenine (HPMPA), 9-(2-phosphonylmethoxyethyl)adenine (PMEA), cyclic (s)-3-hydroxy-2-phosphonylmethoxypropylcytosine (cHPMPC), (2-phosphonylmethoxyethyl)cytosine (PMEC), (2-phosphonylmethoxyethyl)guanine (PMEG), 1-(s)-3-hydroxy-2-phosphonylmethoxypropyluracil ((S)-HPMPU), 9-(s)-3-hydroxy-2-phosphonylmethoxypropylguanine ((S)-HPMPG) (2-phosphonylmethoxyethyl)-2,6-diaminopurine (PMEDAP), and 9-(s)-2-phosphonylmethoxypropyladenine (S)-PMPA).

11. The method of claim 1, wherein the compound is (s)-1-(3-hydroxy-2-phosphonylmethoxypropyl)cytosine (HPMPC) and the amount delivered by a single dosage of the medicament is greater than about 20 μg up to about 50 μg.

12. The method of claim 1, wherein the compound is 9-(s)-(2-phosphonylmethoxy-3-hydroxy-propyl)adenine (HPMPA), and the amount delivered by a single dosage of the medicament is greater than about 40 μg up to about 50 μg.

13. The method of claim 1, wherein the compound is in a composition formulated for intravitreal administration.

14. The method of claim 1, wherein the compound is in a composition formulated for administration by aqueous humor injection, by injection into the external layers of the eye, or topically, whereby contact with the vitreous cavity is effected.

15. The method of claim 1, wherein the compound is in a composition formulated for intraocular administration.

16. The method of claim 1, wherein the compound is (s)-1-(3-hydroxy-2-phosphonylmethoxypropyl)cytosine (HPMPC) and the amount is greater than about 20 μg up to about 50 μg.

17. The method of claim 1, wherein the compound is 9-(s)-(2-phosphonylmethoxy-3-hydroxy-propyl)adenine (HPMPA).

18. The method of claim 1, wherein the compound is cyclic (s)-3-hydroxy-2-phosphonylmethoxypropylcytosine (cHPMPC) or 9-(cyclic(s)-3-hydroxy-2-phosphonylmethoxypropyl)adenine (cHPMPA).

19. The method of claim 1, wherein the amount is about 20 μg up to about 100 μg.

20. The method of claim 1, wherein the compound is administered intravitreally.

21. The method of claim 1, wherein the compound is administered by aqueous humor injection, by injection into the external layers of the eye, or topically, whereby contact with the vitreous cavity is effected.

22. The method of claim 1, wherein the compound is 9-(2-phosphonylmethoxyethyl)adenine (PMEA).

23. The method of claim 1, wherein $R^7$ is $CH_2OH$.

24. The method of claim 2, wherein $R^7$ is $CH_2OH$.

25. The method of claim 1, wherein each of m, n and p is independently 0 or 1.

26. The method of claim 1, wherein the amount of the compound is about 1 μg to about 1000 μg.

27. The method of claim 2, wherein the compound is selected from the group consisting of compounds having the formula:

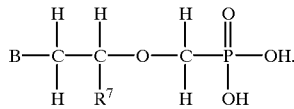

28. The method of claim 1, wherein:
$R^1$ is $CH_2CH(OH)(CH_2)_n$, $CH_2CH(CH_2)_n(OH)$, $CH_2OCH(R^7)$, $CH_2OCH(R^7)(CH_2)_p$, $CH_2OCH(R^7)(CH_2)_pO$ or $O(CH_2)_pCH(R^7)O$;
$R^2$ is OH or $O(CH_2)_rH$;
$R^7$ is OH or $(CH_2)_rOH$;
n is 0–6;
r is 1–6;
p is 0–3; and
m is 0 to 3.

29. The method of claim 4, wherein B is selected from the group consisting of uracil-1-yl, cytosin-1-yl, 5-methylcytosin-1-yl, thymin-1-yl, 5-fluorouracil-1-yl, guanin-9-yl, guanin-7-yl, adenin-3-yl, hypoxanthin-9-yl, 2-methyladenin-9-yl, 2-methylthioadenin-9-yl, 2-aminoadenin-9-yl, 2-aminopurin-9-yl, $N^6$-dimethyladenin-9-yl, 8-bromoadenin-9-yl, 8-hydroxyadenin-9-yl, 6-hydroxylaminopurin-9-yl, 6-hydrazinopurin-9-yl, 6-thiopurin-9-yl, purin-9-yl, and xanthin-9-yl.

30. The method of claim 1, wherein the amount is greater than about 20 μg up to about 100 μg.

31. The method of claim 1, wherein:
$R^1$ and $R^2$ are selected from (i) only, and
$R^1$ is $CH_2CH(OH)(CH_2)_n$, $CH_2CH(CH_2)_n(OH)$, $CH_2OCH(R^7)$, $CH_2OCH(R^7)(CH_2)_p$, $CH_2OCH(R^7)(CH_2)_pO$ or $O(CH_2)_pCH(R^7)O$;
$R^2$ is OH or $O(CH_2)_rH$;
$R^7$ is OH or $(CH_2)_rOH$;
n is 0–6;
r is 1–6;
p is 0–3; and
m is 0 to 3.

32. The method of claim 1, wherein the composition is packaged in a container for delivery of between about 0.50 ml and 0.150 ml and comprises a concentration of the compound of about 10 μg /0.100 ml up to about 100 μg/0.100 ml.

33. The method claim 1, wherein the concentration of the compound is about 10 μg to about 50 μg per 0.100 ml of the composition.

34. The method of claim 4, wherein B is selected from the group consisting of uracil-1-yl, cytosin-1-yl, 5-methylcytosin-1-yl, thymin-1-yl, 5-fluorouracil-1-yl, uracil-3-yl, cytosin-3-yl, 5-methylcytosin-3-yl, thymin-3-yl, 5-fluorouracil-3-yl, guanin-9-yl, guanin-7-yl, guanin-3-yl, adenin-9-yl, adenin-7-yl, adenin-3-yl, hypoxanthin-9-yl, hypoxanthin-7-yl, hypoxanthin-3-yl, 2-methyladenin-9-yl, 2-methyladenin-7-yl, 2-methyladenin-3-yl, 2-methylthioadenin-9-yl, 2-methylthioadenin-7-yl, 2-methylthioadenin-3-yl, 2-aminoadenin-9-yl, 2-aminoadenin-7-yl, 2-amino-adenin-3-yl, 2-aminopurin-9-yl, 2-aminopurin-7-yl, 2-aminopurin-3-yl, $N^6$-dimethyladenin-9-yl, $N^6$-dimethyladenin-7-yl, $N^6$-dimethyladenin-3-yl, 8-bromoadenin-9-yl, 8-bromoadenin-7-yl, 8-bromoadenin-3-yl, 8-hydroxyadenin-9-yl, 8-hydroxyadenin-7-yl, 8-hydroxyadenin-.3-yl, 6-hydroxylaminopurin-9-yl, 6-hydroxylaminopurin-7-yl, 6-hydroxylaminopurin-3-yl, 6-hydrazinopurin-9-yl, 6-hydrazinopurin-7-yl, 6-hydrazinopurin-3-yl, 6-thiopurin-9-yl, 6-thiopurin-7-yl, 6-thiopurin-3-yl, purin-9-yl, purin-7-yl, purin-3-yl, xanthin-9-yl, xanthin-7-yl, and xanthin-3-yl.

35. The method of claim 1, wherein the composition is encapsulated in a liposome.

36. The method of claim 2, wherein the composition is encapsulated in a liposome.

37. The method of claim 1, wherein B is selected from the group consisting of cytosinyl, adeninyl and guaninyl.

* * * * *

UNITED STATES PATENT AND TRADEMARK OFFICE
CERTIFICATE OF CORRECTION

PATENT NO.   : 6,060,463
DATED        : May 9, 2000
INVENTOR(S)  : Freeman

It is certified that error appears in the above-identified patent and that said Letters Patent is hereby corrected as shown below:

Title Page
In the Date of the Patent, second column, line 2, before "Jul.", add a -*-;
Between the Assignee and the Application Number, column 1, line 11 add -[*] Notice: The portion of the term of this patent subsequent to April 4, 2014 has been disclaimed.-;

In the Specification

Column 2,
Line 46, pleace replace "inversive" with --invasive--

Column 5,
Line 52, please replace "40 μ" with --40 μg--

Column 8,
Line 37-38, please replace "$CH_{3-q}$ (hal)q" with --$CH_{3-q}$ (hal)$_q$--

In the Claims
Delete claim 1 and 31 and replace with the following claims:
1. A method for reducing intraocular pressure, comprising administering to the eye an effective amount of a compound of formula I:

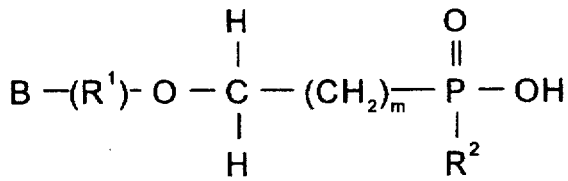

or a pharmaceutically acceptable salt or ester thereof, wherein:
$R^1$ and $R^2$ are (i) or (iii) as follows:
(i) $R^1$ is $CH_2(CH_2)_n$, $CH_2CH(OH)(CH_2)_n$, $CH_2CH(CH_2)_n(OH)$, $CH_2OCH(R^7)$, $CH_2OCH(R^7)(CH_2)_p$, $CH_2OCH(R^7)(CH_2)_pO$ or $O(CH_2)_pCH(R^7)O$;

UNITED STATES PATENT AND TRADEMARK OFFICE
CERTIFICATE OF CORRECTION

PATENT NO. : 6,060,463
DATED : May 9, 2000
INVENTOR(S) : Freeman

It is certified that error appears in the above-identified patent and that said Letters Patent is hereby corrected as shown below:

$R^2$ is OH or $O(CH_2)_rH$;
$R^7$ is H, OH or $(CH_2)_rOH$;
n is 0-6;
r is 1-6;
p is 0-3; and
m is 0 to 3; or
(ii) $R^1$, $R^2$, n, m, r and p are defined as in (i), and $R^1$ and $R^2$ are linked to form a cyclic ester group;
B is a pyrimidine or purine of formula (II):

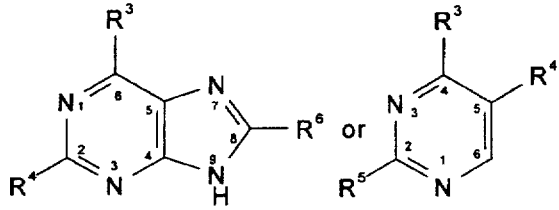

and is selected from the group consisting of pyrimidin-1-yl, pyrimidinyl-3-yl, purin-3-yl, purin-7-yl and purin –9-yl; and
$R^3$, $R^4$, $R^5$ and $R^6$ are independently selected from $NH_2$, alkylamino, aminoalkyl, hydroxyalkyl, hydrazino, H, OH, SH alkylthio, alkyl, alkoxy, alkoxyalkyl, halide, hydroxylamino and $CH_{3-q}(hal)_q$ in which q is 1-3 and hal is a halide; and the amount is effective for lowering intraocular pressure.

31. The method of claim 1, wherein:
$R^1$ and $R^2$ are selected form (i) only, and $R^1$ is $CH_2(OH)(CH_2)_n$, $CH_2CH)(CH_2)_n(OH)$, $CH_2OCH(R^7)(CH_2)_p$, $CH_2OCH(R^7)(CH_2)_pO$ or $O(CH_2)_pCH(R^7)O$;
$R^2$ is OH or $O(CH_2)_rH$;
$R^7$ is H, OH or $(CH_2)_rOH$;
n is 0-6;
r is 1-6;
p is 0-3; and
m is 0 to 3.

UNITED STATES PATENT AND TRADEMARK OFFICE
CERTIFICATE OF CORRECTION

PATENT NO. : 6,060,463
DATED : May 9, 2000
INVENTOR(S) : Freeman

It is certified that error appears in the above-identified patent and that said Letters Patent is hereby corrected as shown below:

Delete Claims 12 and 17 and renumber claims 13 to 16 as 12 to 15, and claims 18 to 21 as 16 to 19.

Add claims 20 and 21 as follows:

20. The method of claim 1, wherein the initial intracular pressure has damaged the optic nerve or reduced the visual field; and the method further comprises; monitoring intraculare pressure after the injection, and then, when the pressure stabilizes, injecting another effective amount of the compound; and repeating the monitoring and injecting step a plurality of times until intracular pressure is at a level whereby further damage to the optic nerve or loss of visual field does not occur.

21. The method of claim 1, wherein the amount administered is effective for lowering introcular pressure to about 90% of its initial value.

Signed and Sealed this

Twenty first Day of August, 2001

*Attest:*

*Attesting Officer*

NICHOLAS P. GODICI
*Acting Director of the United States Patent and Trademark Office*